(12) United States Patent
Wang et al.

(10) Patent No.: US 9,399,708 B2
(45) Date of Patent: Jul. 26, 2016

(54) POLYLACTIDE AND CALCIUM PHOSPHATE COMPOSITIONS AND METHODS OF MAKING THE SAME

(71) Applicants: Tongxin Wang, Berwyn Heights, MD (US); James W. Mitchell, Durham, NC (US)

(72) Inventors: Tongxin Wang, Berwyn Heights, MD (US); James W. Mitchell, Durham, NC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/391,054

(22) PCT Filed: Mar. 8, 2013

(86) PCT No.: PCT/US2013/029858
§ 371 (c)(1),
(2) Date: Oct. 7, 2014

(87) PCT Pub. No.: WO2013/154705
PCT Pub. Date: Oct. 17, 2013

(65) Prior Publication Data
US 2015/0065739 A1  Mar. 5, 2015

Related U.S. Application Data

(60) Provisional application No. 61/623,490, filed on Apr. 12, 2012, provisional application No. 61/623,483, filed on Apr. 12, 2012.

(51) Int. Cl.
| | | |
|---|---|---|
| C07F 9/02 | (2006.01) | |
| C08K 3/32 | (2006.01) | |
| A61L 27/12 | (2006.01) | |
| A61L 27/18 | (2006.01) | |
| A61L 27/58 | (2006.01) | |

(52) U.S. Cl.
CPC . *C08K 3/32* (2013.01); *A61L 27/12* (2013.01); *A61L 27/18* (2013.01); *A61L 27/58* (2013.01); *A61L 2430/02* (2013.01); *C08K 2003/325* (2013.01)

(58) Field of Classification Search
CPC .................................. C08K 9/06; A61L 27/58
USPC .......................................................... 556/405
See application file for complete search history.

(56) References Cited

U.S. PATENT DOCUMENTS

| | | | |
|---|---|---|---|
| 3,066,112 A | 11/1962 | Bowen | |
| 3,274,155 A | 9/1966 | Saunders et al. | |
| 5,007,930 A | 4/1991 | Dorman et al. | |
| 5,085,861 A | 2/1992 | Gerhart et al. | |
| 5,108,755 A | 4/1992 | Daniels et al. | |
| 5,626,861 A | 5/1997 | Laurencin et al. | |
| 5,766,618 A | 6/1998 | Laurencin et al. | |
| 5,866,155 A | 2/1999 | Laurencin et al. | |
| 5,977,204 A | 11/1999 | Boyan et al. | |
| 6,027,742 A | 2/2000 | Lee et al. | |
| 6,287,341 B1 | 9/2001 | Lee et al. | |
| 6,331,312 B1 | 12/2001 | Lee et al. | |
| 6,376,573 B1 | 4/2002 | White et al. | |
| 6,387,414 B1 | 5/2002 | Akashi et al. | |
| 6,649,669 B2 | 11/2003 | Dickens | |
| 7,230,039 B2 | 6/2007 | Trieu et al. | |
| 7,270,813 B2 | 9/2007 | Shimp et al. | |
| 7,670,359 B2 | 3/2010 | Yundt | |
| 7,727,539 B2 | 6/2010 | Laurencin et al. | |
| 7,731,756 B2 | 6/2010 | Maspero et al. | |
| 7,740,794 B1 | 6/2010 | Kumar | |
| 7,758,882 B2 | 7/2010 | Roeder et al. | |
| 7,879,109 B2 | 2/2011 | Borden et al. | |
| 7,959,940 B2 | 6/2011 | Gale et al. | |
| 2002/0127262 A1 | 9/2002 | Akashi et al. | |
| 2003/0082808 A1 | 5/2003 | Guan et al. | |
| 2004/0002770 A1 | 1/2004 | King et al. | |
| 2004/0012335 A1 | 1/2004 | Shon et al. | |
| 2004/0023048 A1 | 2/2004 | Schwartz et al. | |
| 2004/0253290 A1 | 12/2004 | Kim et al. | |
| 2005/0100581 A1 | 5/2005 | Laurencin et al. | |
| 2006/0188712 A1 | 8/2006 | Okada et al. | |
| 2006/0194008 A1 | 8/2006 | Schwartz et al. | |
| 2006/0264531 A1 | 11/2006 | Zhao | |
| 2008/0065228 A1 | 3/2008 | Kim | |
| 2008/0200638 A1 | 8/2008 | Redepenning | |
| 2008/0226547 A1 | 9/2008 | Larsen et al. | |
| 2009/0048358 A1 | 2/2009 | Kim | |
| 2010/0040668 A1 | 2/2010 | Riman et al. | |
| 2010/0131064 A1 | 5/2010 | Redepenning | |

(Continued)

FOREIGN PATENT DOCUMENTS

| | | |
|---|---|---|
| WO | 2011/009228 A1 | 1/2011 |
| WO | 2012/009555 A2 | 1/2012 |
| WO | 2012/078980 A2 | 6/2012 |

OTHER PUBLICATIONS

Zhang et al., Current Applied Physics 5 (2005) 516-518 (Feb. 21, 2005).*

(Continued)

*Primary Examiner* — Porfirio Nazario Gonzalez
*Assistant Examiner* — Kofi Adzamli
(74) *Attorney, Agent, or Firm* — Fitch, Even, Tabin & Flannery, LLP

(57) ABSTRACT

A method is provided for synthesizing polylactide/calcium phosphate composites. In one aspect, an intermediate silanized calcium phosphate material calcium-phosphate/phosphonate is developed to improve the tensile strength of the composite.

11 Claims, 7 Drawing Sheets

(56) References Cited

U.S. PATENT DOCUMENTS

| | | | |
|---|---|---|---|
| 2010/0160467 A1 | 6/2010 | Lee et al. |
| 2010/0179243 A1 | 7/2010 | Liu et al. |
| 2010/0322908 A1 | 12/2010 | Everland et al. |
| 2011/0008460 A1 | 1/2011 | Riman et al. |
| 2011/0069112 A1 | 3/2011 | Matsumoto et al. |
| 2011/0196061 A1 | 8/2011 | Ashman et al. |

OTHER PUBLICATIONS

Zhang et al., Current Applied Physics 5 (2005) 516-518.*
European Patent Office Extended European Search Report dated Oct. 12, 2015 for European Patent Application No. 13775678.9, 7 pages.
C. Deng et al., "Preparation and mechanical property of poly(epsilon-caprolactone)—matrix composites containing nano-apatite fillers modified by silane coupling agents," Journal of Materials Science: Materials in Medicine, Oct. 1, 2010, vol. 21, No. 12, pp. 3059-3064.
C. Deng et al., "Effect of Surface Modification of Nano-Hydroxyapatite Particles on In Vitro Biocompatibility of Poly (epsilon-Caprolactone)—Matrix Composite Biomaterials," International Journal of Polymeric Materials and Polymeric Biomaterials, Nov. 2011, vol. 60, No. 12, pp. 969-978.
PCT International Search Report and Written Opinion of the International Searching Authority dated Mar. 14, 2014 for International Application PCT/US2013/069199, 8 pages.
J. L. Ferracane, "Current Trends in Dental Composites," Critical Reviews in Oral Biology & Medicine, 1995, vol. 6, No. 4, pp. 302-318.
J. P. Santerre et al., "Relation of Dental Composite Formulations to Their Degradation and the Release of Hydrolyzed Polymeric-Resin-Derived Products," Critical Reviews in Oral Biology & Medicine, 2001, vol. 12, No. 2, pp. 136-151.
Tongxin Wang et al., "Synthesis of amphiphilic triblock copolymers with multidentate ligands for surface coating of quantum dots," Presentation No. 0711, Poster Session 2d: Development/Novel Use of Imaging Probes, Sep. 25, 2009, [online]. Retrieved Dec. 7, 2011 from the Internet: <URL: www.wmicmeeting.org/abstracts/data/papers/0711.html>, 2 pages.
Tongxin Wang et al., "High Strength Bioresorbable Composites for Bone Fixation and Repair," Howard University Health Sciences, Research Day 2011, Apr. 15, 2011, 2 pages.
Tongxin Wang et al., "Improve the Strength of PLA/HA Composite Through the Use of Surface Initiated Polymerization and Phosphonic Acid Coupling Agent," Journal of Research of the National Institute of Standards and Technology, Sep. Oct. 2011, vol. 116, No. 5, pp. 785-796.
PCT International Search Report and Written Opinion of the International Searching Authority dated May 20, 2013 for International Application No. PCT/US2013/029858, 18 pages.
S. M. Zhang et al., Interfacial fabrication and property of hydroxyapatite/polylactide resorbable bone fixation composites, Current Applied Physics, 2005, vol. 5, pp. 516-518.
Carmen Kunze et al., Surface modification of tricalcium phosphate for improvement of the interfacial compatibility with biodegradable polymers, Biomaterials, 2003, vol. 24, pp. 967-974.
A. M. P. Dupraz et al., Biocompatibility screening of silane-treated hydroxyapatite powders, for use as filler in resorbable composites, Journal of Materials Science: Materials in Medicine, Dec. 1996, vol. 7, Issue 12, pp. 731-738.
PCT International Search Report and Written Opinion of the International Searching Authority dated May 20, 2013 for International Application No. PCT/US2013/029839, 18 pages.

* cited by examiner

POLYLACTIDE AND CALCIUM PHOSPHATE COMPOSITIONS AND METHODS OF MAKING THE SAME

CROSS-REFERENCE TO RELATED APPLICATIONS

This application is a U.S. national phase application filed under 35 U.S.C. §371 of International Application PCT/US2013/029858, filed Mar. 8, 2013, designating the United States, which claims the benefit of U.S. Provisional Application Ser. No. 61/623,490, filed Apr. 12, 2012, which are incorporated as if fully rewritten herein, and U.S. Provisional Application Ser. No. 61/623,483, filed Apr. 12, 2012, which also is incorporated herein as if fully rewritten.

FIELD

The present application is directed to compositions including calcium phosphate composites and methods for making the same. More particularly, the methods and resulting composites include polylactides and calcium phosphate materials such as tetracalcium phosphate.

BACKGROUND

Bioresorable compositions such as polylactides (PLA) are useful for bone fixation and bone repair and have the advantage of not requiring surgical removal after the bone heals. However, the use of polylactides for bone fixation and bone repair can lead to a variety of undesirable side effects, such as inflammation or allergic reactions.

Many calcium phosphates are excellent candidates for use as bone repair substitutes because of their excellent tissue response and osteooconductivity. Incorporating calcium phosphate ceramics, e.g., hydroxyapatite (HA, $Ca_{10}(PO_4)_6(OH)_2$), tricalcium phosphate (TCP, $Ca_3(PO_4)_2$) and tetracalcium phosphate (TTCP, $Ca_4(PO_4)_2O$), monocalcium phosphate (MCP, $Ca(H_2PO_4)_2$), dicalcium phosphate (DCP, $CaHPO_4$), amorphous calcium phosphate (ACP, $Ca_3(PO_4)_2$), octacalcium phosphate (OCP, $Ca_8H_2(PO_4)_6$), carbonate-substituted apatite (CAP, $Ca_{10-x/2}(PO_4)_{6-x}(CO_3)_x(OH)_2$), and fluoroapatite (FAP, $Ca_{10}(PO_4)_6(OH,F)_2$) into the polymer matrix has been proved to be an effective way to improve the clinical performance.

Combining bioactive calcium phosphates, such as hydroxyapatite (HA), tricalcium phosphate (TCP), tetracalcium phosphate (TTCP), monocalcium phosphate (MCP), dicalcium phosphate (DCP), amorphous calcium phosphate (ACP), octacalcium phosphate (OCP), carbonate-substituted apatite (CAP), fluoroapatite (FAP) and other halogen-substitute apatite (XAP) with PLA yields a composition similar to the composition found in bone and teeth. Polylactide/calcium phosphate composites make an implant more osteoconductive and aides in lessening the side-effect of PLA by neutralizing acidic bio-degraded by-products of PLA. Although HA and TCP can be used to consume acidity, they are not suitable for buffering at pH 7.4 due to the complex phenomenon of dissolution-reprecipitation of the solid phase. Because of the slow dissolution, it generally takes a long time for the composite to degrade.

Polylactide/calcium phosphate composites have the potential of improving clinical bone healing. However, current polylactide/calcium phosphate composites have a significant setback due to its mechanical weakness. Due to the weak interfacial strength between inorganic particulate and PLA matrix, as a result, brittle fracture behavior is observed in this biocomposite system.

The current methods of synthesizing polylactide/calcium phosphate composites mostly consist of direct blending or mixing of the polylactide with calcium phosphate particles. This creates weak interfacial adhesion between PLA (hydrophobic) and calcium phosphate (hydrophilic) moieties along with agglomeration or clumping of calcium phosphate particles.

SUMMARY

It has been unexpectedly found that polylactide/calcium phosphate material may be prepared whereby the calcium phosphate material having a general formula of $Ca_p(PO_q)_yX_z$, where p=1-10, q=1-10 and z=1-5 and where X may be OH, O, $CO_3$, F, Cl, Br, in particular hydroxyapatite (HA), tricalcium phosphate (TCP), tetracalcium phosphate (TTCP), monocalcium phosphate (MCP), dicalcium phosphate (DCP), amorphous calcium phosphate (ACP), octacalcium phosphate (OCP), carbonate-substituted apatite (CAP), fluoroapatite (FAP) and other halogen-substitute apatite (XAP), is modified prior to coupling with the polylactide having a general formula of —$(OCR_1R_2CO)_n$— or —$(R_3COO)_n$—, where $R_1$, $R_2$, $R_3$ can be any of H, alkyl less than C10 and other substitutes and n=1-4. Other degradable polymer materials besides polylactide may also be used such as polycaprolactone (PCL), polyglycolide (PGA) and PLGA (polylactide-co-glycolide), polyhydroxybutyrate, poly(hydroxyvalerate, poly(carbonates), polyphosphazene, polyanhydrides, polycaprolactone, polyurethane or other polyesters and natural origin degradable polymers such as cellulose, starch, gelatin, chitosan, peptides and their derivatives.

In one form, the calcium phosphate material is protonated with an acid, and after protonation, combined with a silane material having a general formula of $(R_1O)(R_2O)(R_3O)Si$—$R_4$—Y, where Y can be OH, NH2, SH, Cl; $R_1$, $R_2$, $R_3$ can be the same or different from alkyl (C1-C10), $R_4$ is alkyl (C1-C20), the RO on the silane reacting with the phosphate which is protonated to form an intermediate silanized calcium phosphate material, for example silanized tetracalcium phosphate material. The intermediate silanized calcium phosphate material may then be combined with a lactide material having a general formula of —$(OCR_1R_2CO)_n$— or —$(R_3COO)_n$—, where $R_1$, $R_2$, $R_3$ can be any of H, alkyl less than C10 and other substitutes and n=1-4 to form the polylactide/calcium phosphate matrix material, the reaction between the intermediate and the silane initiated by Y on the silane. The polylactide/calcium phosphate matrix material has a tensile strength that is at least 1.3 times the tensile strength of a polylactide/calcium phosphate material prepared without combining the silane with the calcium phosphate material.

In particular, tetracalcium phosphate (TTCP) has relatively desirable bioactivity and is a soluble form of calcium phosphate. TTCP was also proved to be biocompatible and possessed osteoconductive properties. Because of the higher Ca/P ratio of TTCP compared with HA, complete hydration is expected to form calcium hydroxide and a strong alkaline pH value. The degradation alkaline functionality could compensate the release of acidic monomers from biodegradable PLA, thus improving tissue compatibility.

Combining the protonated calcium phosphate source with a silane material may further include pyromellitic dianhydride which may improve the storage modulus of the polylactide/calcium phosphate matrix material. It is believed that such polylactide/calcium phosphate composite prepared from an intermediate silanized calcium phosphate material may have increased tensile strength compared to a polylactide/calcium phosphate material that has not been modified with a silane material.

In one form, protonated calcium phosphate material is combined with a silane material to form an intermediate silanized calcium phosphate material. The intermediate silanized calcium phosphate material may then be combined with PLA. Further, an acid anhydride material, such as pyromellitic dianhydride may be combined to the intermediate silanized calcium phosphate material along with the PLA and/or after addition of the PLA. Additionally, other biocompatible acid anhydrides may also be used, such as diacid anhydrides and triacid anhydrides.

According to one form the protonated calcium phosphate source is modified with the silane coupling containing material to increase the dispersion of calcium phosphate in an intermediate silanized calcium phosphate material or matrix. In one form, the intermediate silanized calcium phosphate material results in P—O—Si structures, where a plurality of the —OH groups of calcium phosphate have been reacted and the silane coupling containing material and covers the calcium phosphate surface, this increases the stability of a tetracalcium matrix in suspension.

The method may also include the step of combining calcium phosphate material with a silane material which further includes combining pyromellitic dianhydride (PMDA) with the silanized calcium phosphate material.

In one form the silane coupling material includes N-(2-aminoethyl)-3-aminoproplytrimethoxysilane (AEAPS). According to one form, the silane coupling material can include any other silane agent with a general formula of $(R_1O)(R_2O)(R_3O)Si—R_4—Y$ where Y can be OH, $NH_2$, SH, Cl; $R_1$, $R_2$, $R_3$ can be the same or different C1-C10 alkyl, $R_4$ is C1-C20 alkyl. In this regard, in one form, the calcium phosphate source, preferably tetracalcium phosphate is suspended in a phosphoric acid within alcohol, acetone, ether, preferable an ethanol phosphoric acid.

The polylactide/calcium phosphate produced by combining the calcium phosphate source with the silane coupling containing material creates a P—O—Si structure on the surface of the intermediate silanized calcium phosphate material.

In one form, the method of synthesis may provide increased tensile strength when compared to that of polylactide alone.

By one approach, the composition comprises significantly higher amount of polylactide covalently attached to calcium phosphate than that of current compositions produced by conventional methods.

DETAILED DESCRIPTION

Figure 1:
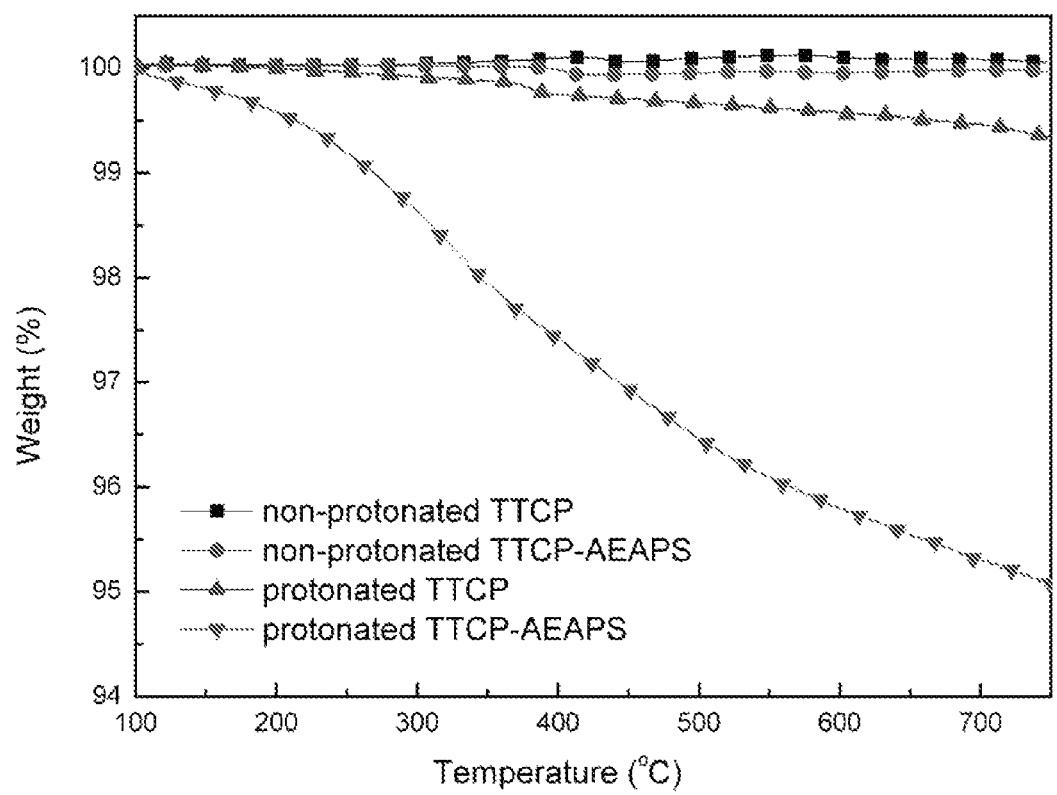
FIG. 1 illustrates X thermogravimetric analysis (TGA) curves of various tetracalcium phosphate composites.

Described herein are methods and compositions comprising polylactide/calcium phosphate composites. In one form, the general method provides synthesis of polylactide/calcium phosphate by combining a protonated calcium phosphate material having a general formula of $Ca_p(PO_4)_qX_z$, where p=1-10, q=1-10 and z=1-5, where X may be OH, O, $CO_3$, F, Cl, Br with a silane material having a general formula of $(R_1O)(R_2O)(R_3O)Si—R_4—Y$, where Y can be OH, NH2, SH, Cl; $R_1$, $R_2$, $R_3$ can be the same or different C1-C10 alkyl, $R_4$ is C1-C20 alkyl to yield an intermediate grafted silanized calcium phosphate material that improves dispersion of calcium phosphate in a matrix. It should be noted that when referring to a composite material, the material includes lactide/modified calcium phosphate material along with additional lactide material. In other words, the lactide/modified calcium phosphate material is in a matrix with the additional lactide material.

In one aspect, combining the protonated calcium phosphate source with a silane coupling containing material may further include combining pyromellitic dianhydride which may improve the storage modulus of the polylactide/calcium phosphate matrix material. It is believed that such a composite polylactide/calcium phosphate prepared from an intermediate grafted silanized calcium phosphate matrix material may have increased tensile strength compared to a polylactide/calcium phosphate material that has not been modified with a silane coupling containing material.

The calcium phosphate material may include a variety of materials such as $Ca_p(PO_4)_qX_z$, where p=1-10, q=1-10 and z=1-5 and where X may be OH, O, $CO_3$, F, Cl, Br including protonated phosphate (e.g., $HPO_4^{2-}$, $H_2PO_4^-$), in particular hydroxyapatite (HA), tricalcium phosphate (TCP), tetracalcium phosphate (TTCP), monocalcium phosphate (MCP), dicalcium phosphate (DCP), amorphous calcium phosphate (ACP), octacalcium phosphate (OCP), carbonate-substitute apatite (CAP), fluoroapatite (FAP) and other halogen-substitute apatite (XAP), preferable protonated tetracalcium phosphate. The protonated calcium phosphate is prepared by treatment with an acid, exemplary acids include phosphoric acid, phosphonic acid, sulfonic acid, carboxylic acid, preferable diluted phosphoric acid. In one form, a range of the molar ratio of acid phosphate in calcium phosphates can be 1:10 or less, preferably around 1:50.

The silane material may include materials having the general formula $(R_1O)(R_2O)(R_3O)Si—R_4—Y$, where Y can be OH, NH2, SH, Cl; $R_1$, $R_2$, $R_3$ can be the same or different from alkyl (C1-C10) $R_4$ is alkyl (C1-C20), such as N-(2-aminoethyl)-3-aminoproplytrimethoxysilane (AEPS). The range of silane can be 1:2 or less, preferably around 1:20 in relation to calcium phosphate.

The lactide material may include materials having the general formula $—(OCR_1R_2CO)_n—$ or $—(R_3COO)_n—$, where $R_1$, $R_2$, $R_3$ can be any of H, alkyl less than C10 and other substitutes. Further degradable polymer materials that may be used include polycaprolactone (PCL), polyglycolide (PGA) and PLGA (polylactide-co-glycolide), polyhydroxybutyrate, poly(hydroxyvalerate, poly(carbonates), polyphosphazene, polyanhydrides, polyurethane or other polyesters and natural origin degradable polymers such as cellulose, starch, gelatin, chitosan, peptides and their derivatives. The amount of the lactide material may range from 1% to about 99% of the overall composite composition. In one form, the amount of lactide is about 50% of the overall composite composition.

In one embodiment, grafting by silanization at the surface of the calcium phosphate is prepared by mixing the protonated calcium phosphate and a silane material (total 50 g with a weight ratio of slime and calcium phosphate 1:10), exemplary coupling materials are $(R_1O)(R_2O)(R_3O)Si-R_4-Y$, where Y can be OH, NH2, SH, Cl; $R_1$, $R_2$, $R_3$ can be the same or different from alkyl (C1-C10), $R_4$ is alkyl (C1-C20), preferably AEAPS in an anhydrous solvent, such as toluene, acetone, ether (200 mL), preferably toluene mixed with a gas used to displace oxygen-and moisture-containing air, an exemplary gas is nitrogen or argon. The silanized calcium phosphate was filtered and repeatedly washed with an anhydrous alcohol, acetone, ether, exemplary anhydrous solutions include alcohols, preferably ethanol (50 mL three times), for the complete removal of non-bound coupling agent. The silanized calcium phosphate was dried in an oven for 8-72 hours, preferably 24 hours at 50-150° C., preferably 110° C.

In one aspect, polylactide/calcium phosphate was prepared by melt compound at 200-250° C., preferably 230° C. for PLA with a screw speed of 10-100 rpm, preferably 50 rpm. Silanized calcium phosphate was mixed with polylactide or analougs, e.g., PGA, PLGA, PCL in a weight ratio to calcium phosphate 1%-99%, preferably 50%, for 1-30 minutes. Additionally, PMDA was further added and mixed in 0%-5% wt, preferably 0.2%. The samples were injection molded in an injection-molding machine, such as Polylab OS RheoDrive 7 (Germany). The injection and holding time were set as 15 seconds and 30 seconds, with a mold temperature of 50-120° C., preferably 85° C.

Exemplary methods for making the composite will be described below.

Surface Protonation of Tetracalcium Phosphate (TTCP)

Tetracalcium phosphate was stirred with dilute anhydrous alcohol phosphoric acid (50:1 w/w) at room temperature for about 1 hour and then subsequently washed with anhydrous ethanol. The protonated TTCP particles were dried in the oven overnight at about 100° C. Other acid to activate calcium phosphate can be carbosxylic acid, sulfonic acid, phosphonic acid and sulfuric acid, hydrochloric acid, acetic acid, and any other acid.

Grafting of N-(2-aminoethyl)-3-aminoproplytrimethoxysilane (AEAPS) on the Surface of TTCP The silanization reaction was performed under reflux using a suspension of protonated tetracalcium phosphate and N-(2-aminoethyl)-3-aminoproplytrimethoxysilane in about 2:1 ratio in anhydrous toluene with continuous stirring under argon atmosphere at about 110° C. for about 24 hours. The silanized. tetracalcium phosphate (TTCP-AEAPS) was filtered and washed with anhydrous ethanol for complete removing of non-bounded coupling agent, TTCP-AEAPS powders were dried in the oven overnight at about 100° C.

Preparation of PLA/TTCP Composites

The PLA/TTCP composites were prepared by melt compounding using a Haake Polylab OS RheoDrive 7 (Germany) at about 230° C. with a screw speed of about 50 rpm. Prior to melt processing, TTCP and TTCP-AEAPS were dried in a vacuum oven overnight at about 100° C. The ingredients of desired proportions of PLA and TTCP were incorporated into the mixer for about 3 minutes, then desired PMDA (0.2 wt %) was put into the mixer for about another 4 minutes. The samples were injection molded into standard samples in an injection-molding machine (Haake Minijet II, Thermo Fisher Scientific, Co. Ltd, Germany) at about 230° C. The injection and holding time were set at about 15 s and 30 s, respectively. The injection pressure and holding pressure were 85 MPa and 15 MPa, with the mold temperature of about 85° C.

In one aspect, FTIR spectrometry was performed with KBr pellets using a Thermo Nicolet 6700 FTIR spectrum analyzer in the wavenumber range of 4000 to 650 cm$^{-1}$. Spectra were signal averaged over 16 scans at a resolution of 4 cm$^{-1}$. The amount of surface grafted compound was characterized by TGA (Perkin-Elmer, Pyris 1) in nitrogen atmosphere from about 100° C. to about 750° C. at a heating rate of about 20° C./min with airflow of about 80 mL/min. The amount of slime on the surface of TTCP was supposed to be the weight loss percentage. An SEM (JSM-6700F field emission Scanning Electron Microscope) was used to investigate the morphology of the fracture surface. Prior to the SEM examination, samples were submerged in liquid nitrogen for about 30 minutes and broken to expose the internal structure for SEM studies. The tensile property was characterized at room temperature according to ISO 527 on an Instron 3365 universal test machine (Instron Corporation, USA). The cross-head speed of the apparatus was 5 mm/min. The bending property was measured at room temperature according to ISO 178 on an Instron 3365 machine at a bending speed of about 1 mm/min. The mechanical data were obtained by averaging of three specimens. Dynamic mechanical analysis (DMA Q800, TA Instruments) was performed with a single-cantilever clamp on sample bar measuring 35×4×2 mm3. A temperature ramp experiment was conducted with amplitude of 15 μm from −50° C. to 150° C. at a heating rate of 3° C./min with a constant frequency of 1 Hz.

EXAMPLES

Example 1

Grafting of AEAPS on the Surface of TTCP

AEAPS can directly react with hydroxyl through —OR group of the silane derivatives. Amino groups of the silane derivatives may further react towards the terminal carboxylic groups. PMDA is believed to react with amino group of the AEAPS and terminal hydroxyl groups of PLA. As a basis for the silanization at the surface of TTCP, protonation the TTCP surface was necessary. The treatment of TTCP with diluted phosphoric acid led to the formation of calcium hydrogen phosphate at the surface of TTCP. As shown in FIG. 1, there is almost no weight loss for non-protonated TTCP and non-protonated TTCP-AEAPS even at 750° C. It is believed that AEAPS could hardly be grafted onto the surface of TTCP before the surface protonation procedure. After surface protonation, AEAPS was immobilized on the surface of TTCP. The protonated TTCP showed high thermal stability and displayed about 0.4% weight loss even at 750° C. For TTCP-AEAPS, it had appreciable weight loss, which was attributed to the decomposition of the grafted AEAPS. There was almost 5 wt % AEAPS immobilized on the surface of TTCP.

Figure 2:
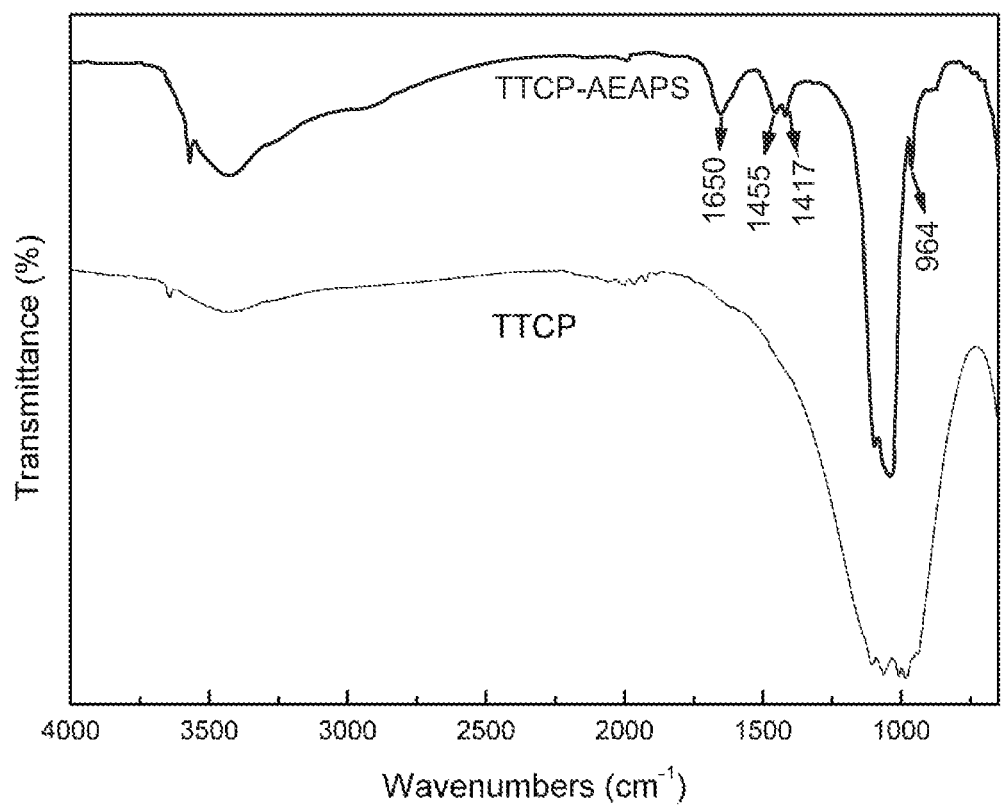
FIG. 2 illustrates FTIR spectrometry of tetracalcium phosphate and intermediate silanized tetracalcium phosphate.

FTIR was used to indicate that AEAPS is grafted on the surface of TTCP after silanization (FIG. 2). The broad strong bands around 3700~3200 cm$^{-1}$ are assigned to the hydroxyl stretching vibration of TTCP. The bond in 1700~730 cm$^{-1}$ region corresponds to the characteristic peak of TTCP. After the silanization, new characteristic peaks were observed. The band around 1735-1550 cm$^{-1}$ is ascribed to hydroxyl bending after the protonation of the TTCP surface. The characteristic of CH2 bending appears around 1490~1380 cm$^{-1}$. The shoulder peak around 1570 cm$^{-1}$ attributed to N—H bending is not observed because of the low content of AEAPS on TTCP surface and overlapping of broad strong hydrogen band around 1650 cm$^{-1}$. It is also noticed that a special peak at 964 cm$^{-1}$ exists neither in TTCP nor in AEAPS spectrum.

Figure 3:
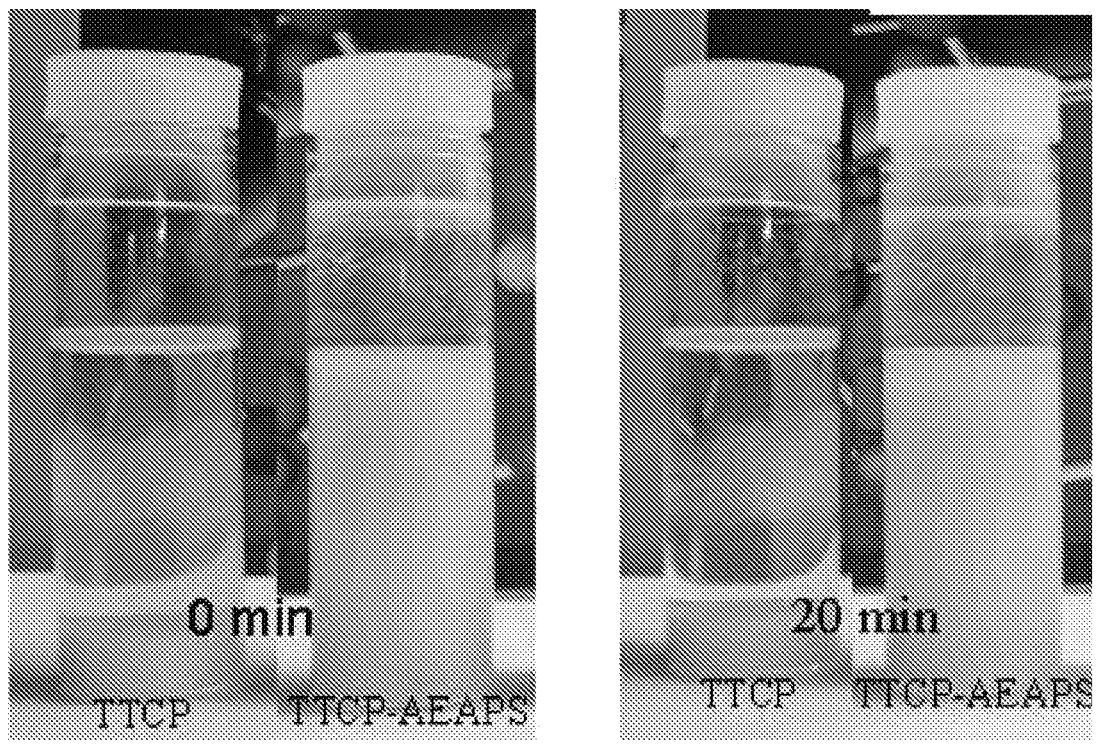
FIG. 3 illustrates photographs of tetracalcium phosphate and intermediate silanized tetracalcium phosphate dispersed in dichloromethane.

The structure P—O—Si resulting from the coupling reaction between the AEAPS and TTCP may contribute to this newly emerged peak at 964 cm$^{-1}$. The covalent bond was generated between TTCP and AEAPS. 0.5 g TTCP and TTCP-AEAPS were dispersed into 4 mL dichloromethane, respectively. The suspensions were magnetic stirred vigorously for 10 minutes. After that TTCP deposited to the bottom immediately, while the TTCP-AEAPS solution was even stable after 20 minutes (FIG. 3). Neat TTCP tends to form large agglomerates. After silanization, most of hydroxyl groups of TTCP have been reacted and AEAPS was covered the TTCP surface, which could increase the stability of the suspension.

Example 2

Mechanical Property

Figure 4:
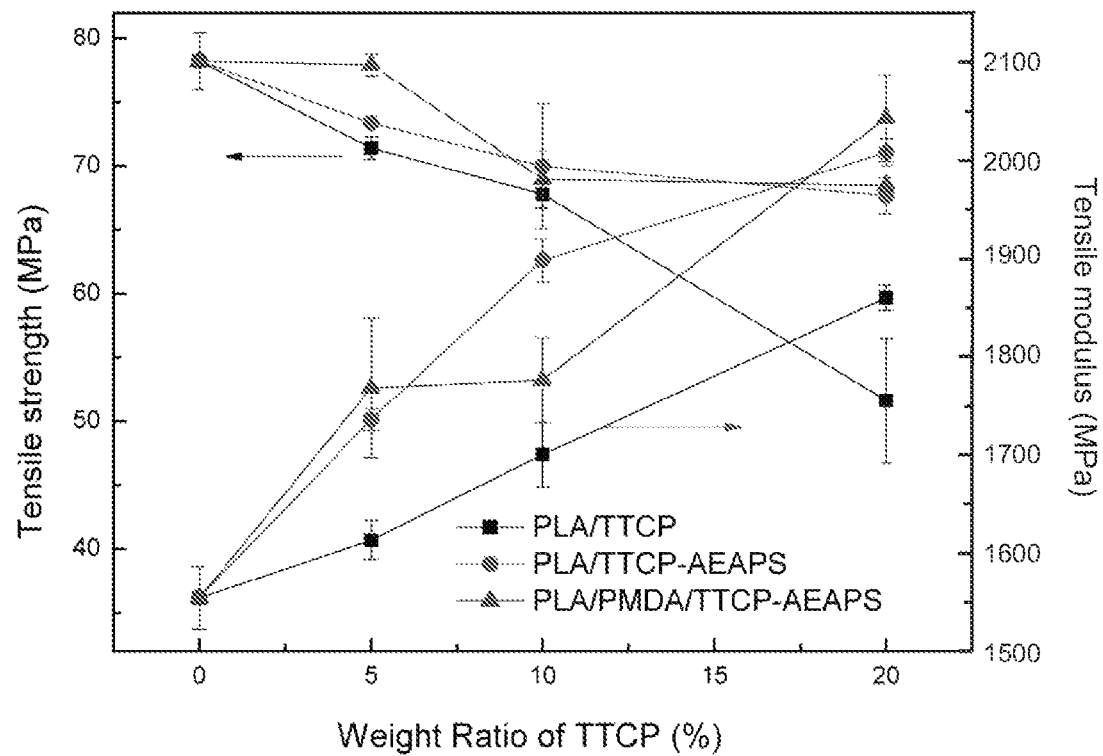
FIG. 4 illustrates tensile properties of various forms of polylactide/tetracalcium phosphate composites.

It is believed that due to the presence of AEAPS on the surface, the interfacial strength was improved. The mechanical strength of PLA/TTCP-AEAPS composites was higher than that of PLA/TTCP composites with different contents (FIG. 4). For example, the tensile strength was 68.4 MPa for PLA/TTCP-AEAPS composite (20 wt %—meaning the overall composite material includes 20 wt % modified TTCP-AEAPS). However, it dropped to 51.5 MPa, when 20 wt % TTCP was incorporated into the matrix. The improved coupling leads to areas with ductile stretched polymer at the interface between PLA and TTCP. The surface modification may contribute to improving the interfacial adhesion. It is well known that there is big agglomeration when inorganic fillers are incorporated into polymeric materials especially at a high loading. Therefore, loosened clusters of TTCP could lead to breakdown of the composite.

The strength dropped linearly for PLA/TTCP composites. Better interfacial adhesion between filler and polymer matrix may help improve load transfer. The tensile strength was 684 MPa even with 20 wt % (meaning the overall composite material includes 20 wt % modified TTCP-AEAPS) TTCP-AEAPS incorporation, which was 32% increase than of PLA/TTCP composite (20 wt %—meaning the overall composite material includes 20 wt % non-modified TTCP). In order to fulfill the various requirements, high loading of calcium phosphate cements are required.

The difference of tensile strength among the composites became smaller at high loading with and without PMDA incorporation. As shown in FIG. 3, the tensile modulus increased for all the composites. After incorporating TTCP-AEAPS into the matrix (20 wt %—meaning the overall composite material includes 20 wt % modified TTCP-AEAPS), the tensile modulus increased to 2000 MPa from 1550 MPa of pure PLA. It was believed that the functional particle could make contribution to improving the modulus, which might be attributed to good interfacial property. However, no remarkable difference was observed when PMDA (0.2 wt %—meaning the overall composite material included 0.2 wt % PMDA) was incorporated into the matrix. It might because there was limited reaction between anhydride and amino group occurred during the compounding process.

Figure 5:
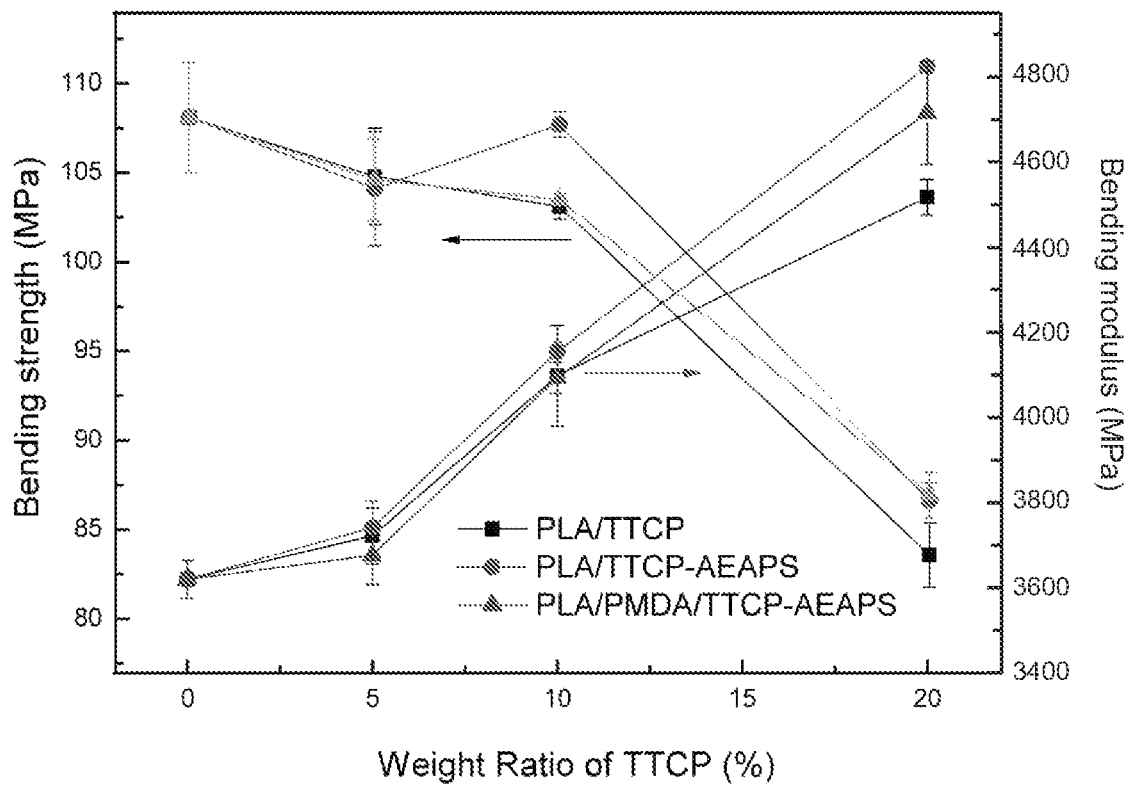
FIG. 5 illustrates bending properties of various forms of polylactide/tetracalcium phosphate composites.

Regarding bending of the materials, TTCP may also contribute to improving the modulus but decreasing the strength (FIG. 5). Because of the large agglomeration at high loading, the bending strength dropped even for the PLA/TTCP-AEAPS composites. The particle would debond easily to enable crack initiation and propagation. Increasing TTCP fraction increases the agglomeration, and more cracks can form and develop, thus decreasing the strength of the composites. There was no obvious difference among the composites, suggesting that interfacial strength between the particles and matrix was not strong enough. it has been reported that the surface modification method could improve the interfacial adhesion, but these interactions were weak during the bending study. Though the strength of the composites was a little lower compared to that of pure PLA, the composite could be used in clinic.

Example 3

Dynamic Mechanical Property of PLA/TTCP Composites

Figure 6B:
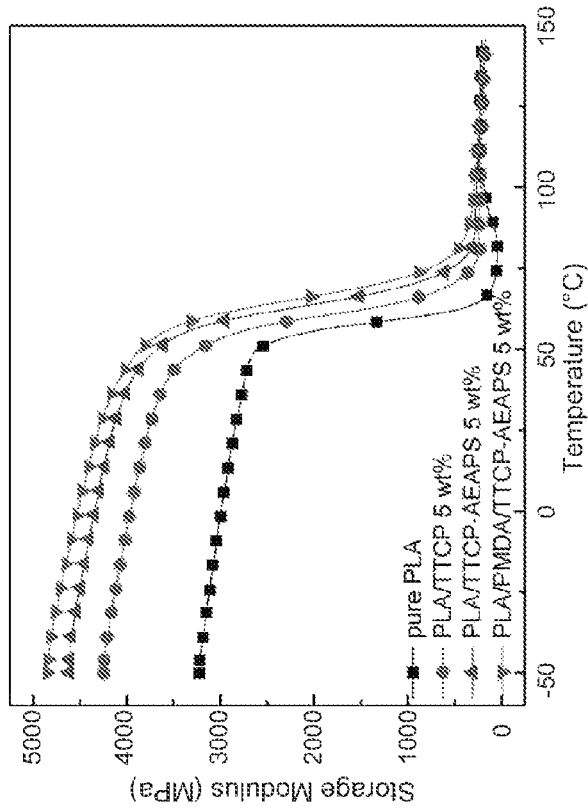
FIGS. 6A and 6B illustrate dynamic mechanical property curves of various forms of polylactide/tetracalcium phosphate composites.
Figure 6A:
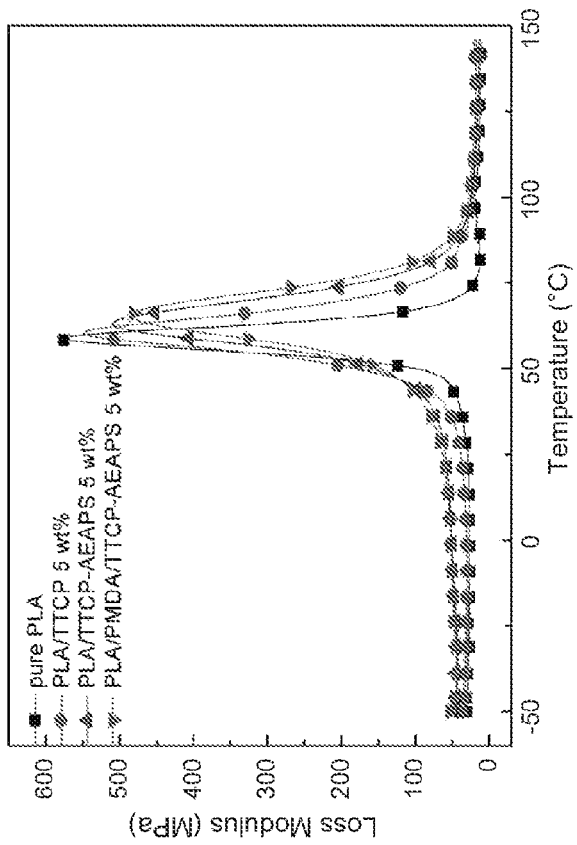

FIG. 6 shows the dynamic storage modulus of PLA and PLA/TTCP composites (5 wt %) over a temperature range of −50 to 150° C. It was found that the storage modulus increased with incorporation of filler over the entire temperature range. At −50° C., the storage modulus for PLA was 3.21×109 Pa, which decreased with the increasing temperature; at the glass-transition temperature (Tg=58.9° C.) it dropped significantly. This is attributed to insufficient thermal energy to overcome the potential barrier for transitional and rotational motions of segments of the polymer molecules in the glassy region. Whereas above Tg, the thermal energy becomes comparable to the potential energy barriers to the segmental motions.

Figure 7A:
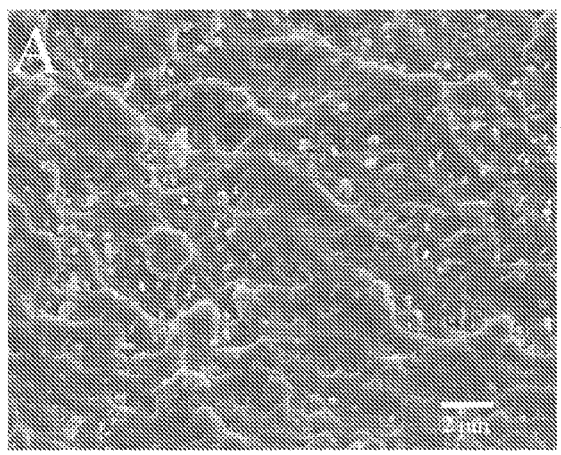
FIGS. 7A and 7B illustrate scanning electron microscope images of various forms of polylactide/calcium phosphate composites.
Figure 7B:
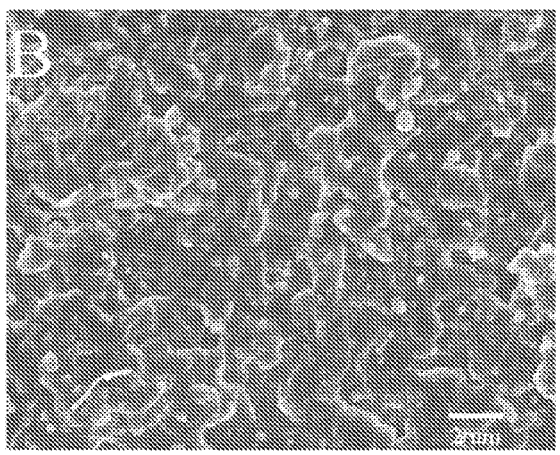

For PLA/TTCP composite (5 wt %—meaning the overall composite material includes 20 wt % modified TTCP-AEAPS), notable enhancement of the storage modulus (32% increase) was observed in the lower temperature range, indicating that TTCP had remarkable influence on the elastic properties of the PLA matrix. By incorporating TTCP-AEAPS (5 wt %) into the matrix, the storage modulus was 4.62×10$^9$ Pa, which is 44% higher than that of neat PLA. It is believed that AEAPS was beneficial for the compatibility with the polar polymer matrix (FIG. 7A). When 0.2 wt % PMDA (meaning the overall composite material included 0.2 wt. % PMDA) was incorporated into the composites, the storage modulus was increased to 4.88×109 Pa (51% increase). The anhydride could react with the amino group which was grafted on the surface of TTCP, thus leading to a better interfacial property (FIG. 7B). The anhydride might react with the terminal hydroxyl group of PLA, the interfacial property was improved. These two factors made contribution to the additional increase of the storage modulus. However, the degree of reaction between amino group and anhydride might be low and the increase was not very large. Tg increased from 63.2° C. for PLA/TTCP-AEAPS (5%—meaning the overall composite material includes 5 wt % modified TTCP-AEAPS) to 65.5° C. when PMDA was incorporated into the composite (FIG. 6B), signifying that a better interface was generated.

The foregoing descriptions are not intended to represent the only forms of the compositions and methods according to the present application. The percentages provided herein are by weight unless stated otherwise. Changes in form and in proportion of components, as well as the substitution of equivalents, are contemplated as circumstances may suggest or render expedient. Similarly, while compositions and methods have been described herein in conjunction with specific embodiments, many alternatives, modifications, and variations will be apparent to those skilled in the art in light of the foregoing description.

What is claimed is:

1. A method for preparing a polylactide/calcium phosphate containing material comprising the steps of:

combining a calcium phosphate material having a general formula of $Ca_p(PO_4)_qX_z$, where p=1-10, q=1-10 and z=1-5 and where X may be O, $CO_3$, F, Cl, Br with a silane material haying a general formula of $(R_1O)(R_2O)(R_3O)Si-R_4-Y$, where Y can be OH, NH2, SH, Cl; $R_1$, $R_2$, $R_3$ can be the same or different C1-C10 alkyl, $R_4$ is C1-C20 alkyl, to form an intermediate silanized calcium phosphate material; and combining polymer selected from the group consisting of a lactide material haying a general formula of $-(OCR_1R_2CO)_n-$ or $-(R_3COO)_n-$, where $R_1$, $R_2$, $R_3$ can be any of H, alkyl less than C10, polyglycolide, polylactide-co-glycolide, polycaprolactone and mixtures thereof with the intermediate silanized calcium phosphate material to form the polylactide/calcium phosphate material initiated.

2. The method of claim 1 wherein the step of combining the calcium phosphate material with a silane material reacts hydroxyl groups on the surface of the calcium phosphate material through alkoxy groups of the silane material to form the intermediate silanized calcium phosphate material.

3. The method of claim 1 wherein the step of combining the calcium phosphate material with the silane material creates a P—O—Si structure in the intermediate silanized calcium phosphate material.

4. The method of claim 1 wherein the calcium phosphate material surface is protonated.

5. A method for preparing a polylactide/calcium phosphate containing material comprising the steps of:
combining a calcium phosphate material having a general formula of $Ca_p(PO_4)_qX_z$, where p=1-10, q=1-10 and z=1-5 and where X may be OH, O, $CO_3$, F, Cl, Br with a silane material having a general formula of $(R_1O)(R_2O)(R_3O)Si-R_4-Y$, where Y can be OH, NH2, SH, Cl; $R_1$, $R_2$, $R_3$ can be the same or different C1-C10 alkyl, $R_4$ is C1-C20 alkyl, to form an intermediate silanized calcium phosphate material;

combining polymer selected from the group consisting of a lactide material having a general formula of $-(OCR_1R_2CO)_n-$ or $-(R_3COO)_n-$, where $R_1$, $R_2$, $R_3$ can be any of H, alkyl less than C10, polyglycolide, polylactide-co-glycolide, polycaprolactone and mixtures thereof with the intermediate silanized calcium phosphate material to form the polylactide/calcium phosphate material initiated; and wherein combining calcium phosphate material with a silane material includes combining pyromellitic dianhydride with the calcium phosphate material.

6. The method of claim 1 wherein the calcium phosphate material is suspended in an anhydrous solvent.

7. A method for preparing a polylactide/calcium phosphate containing material comprising the steps of:
combining a calcium phosphate material having a general formula of $Ca_p(PO_4)_qX_z$, where p=1-10, q=1-10 and z=1-5 and where X may be OH, O, $CO_3$, F, Cl, Br with a silane material having a general formula of $(R_1O)(R_2O)(R_3O)Si-R_4-Y$, where Y can be OH, NH2, SH, Cl; $R_1$, $R_2$, $R_3$ can be the same or different C1-C10 alkyl, $R_4$ is C1-C20 alkyl, to form an intermediate silanized calcium phosphate material;

combining polymer selected from the group consisting of a lactide material having a general formula of $-(OCR_1R_2CO)_n-$ or $-(R_3COO)_n-$, where $R_1$, $R_2$, $R_3$ can be any of H, alkyl less than C10, polyglycolide, polylactide-co-glycolide, polycaprolactone and mixtures thereof with the intermediate silanized calcium phosphate material to form the polylactide/calcium phosphate material initiated; and wherein the silane material includes N-(2-aminoethyl)-3-aminoproplytrimethoxysilane.

8. The method of claim 1 wherein the intermediate silanized calcium phosphate is filtered and washed with anhydrous solvent for removal of non-bounded coupling agent.

9. The method of claim 1 wherein the calcium phosphate material is tetracalcium phosphate.

10. A method for preparing a polylactide/calcium phosphate containing material comprising the steps of:
combining a calcium phosphate material having a general formula of $Ca_p(PO_4)_qX_z$, where p=1-10, q=1-10 and z=1-5 and where X may be O, $CO_3$, F, Cl, Br with a silane material haying a general formula of $(R_1O)(R_2O)(R_3O)Si-R_4-Y$, where Y can be OH, NH2, SH, Cl; $R_1$, $R_2$, $R_3$ can be the same or different C1-C10 alkyl, $R_4$ is C1-C20 alkyl, to form an intermediate silanized calcium phosphate material; and combining polymer selected from the group consisting of a biodegradable polymer selected from the group consisting of polyhydroxybutyrate, poly(hydroxyvalerate, poly(carbonates), polyphosphazene, polyanhydrides, polyurethane, polyesters cellulose, starch, gelatin, chitosan, peptides and mixtures thereof with the intermediate silanized calcium phosphate material to form the polylactide/calcium phosphate material.

11. A method for preparing a polylactide/calcium phosphate containing material comprising the steps of:
combining a calcium phosphate material selected from the group consisting of tricalcium phosphate, tetracalcium phosphate, monocalcium phosphate, dicalcium phosphate, amorphous calcium phosphate, octacalcium phosphate with a silane material having a general formula of $(R_1O)(R_2O)(R_3O)Si-R_4-Y$, where Y can be OH, NH2, SH, Cl; $R_1$, $R_2$, $R_3$ can be the same or different from alkyl (C1-C10), $R_4$ is alkyl (C1-C20), to form an intermediate silanized calcium phosphate material; and combining polymer selected from the group consisting of a lactide material having a general formula of $-(OCR_1R_2CO)_n-$ or $-(R_3COO)_n-$, where $R_1$, $R_2$, $R_3$ can be any of H, alkyl less than C10, polyglycolide, polylactide-co-glycolide, polycaprolactone and mixtures thereof with the intermediate silanized calcium phosphate material to form the polylactide/calcium phosphate material initiated.

* * * * *